(12) United States Patent
Goldan et al.

(10) Patent No.: US 8,877,257 B2
(45) Date of Patent: Nov. 4, 2014

(54) METHODS AND COMPOSITIONS FOR TREATING CONDITIONS ASSOCIATED WITH INFECTION AND/OR INFLAMMATION

(75) Inventors: Keith Goldan, Downingtown, PA (US); Claire Sampson, Doylestow, PA (US)

(73) Assignee: Puricore, Inc., Malvern, PA (US)

( * ) Notice: Subject to any disclaimer, the term of this patent is extended or adjusted under 35 U.S.C. 154(b) by 1150 days.

(21) Appl. No.: 12/523,507

(22) PCT Filed: Jan. 16, 2008

(86) PCT No.: PCT/US2008/051208
§ 371 (c)(1),
(2), (4) Date: May 28, 2010

(87) PCT Pub. No.: WO2008/089268
PCT Pub. Date: Jul. 24, 2008

(65) Prior Publication Data
US 2010/0285151 A1    Nov. 11, 2010

Related U.S. Application Data

(60) Provisional application No. 60/885,122, filed on Jan. 16, 2007.

(51) Int. Cl.
*A01N 59/08* (2006.01)
*A61K 33/14* (2006.01)
*A61K 33/20* (2006.01)

(52) U.S. Cl.
CPC ..................................... *A61K 33/20* (2013.01)
USPC ......................................................... 424/661

(58) Field of Classification Search
None
See application file for complete search history.

(56) References Cited

U.S. PATENT DOCUMENTS

| | | |
|---|---|---|
| 2002/0160053 A1 | 10/2002 | Yahagi et al. |
| 2003/0185704 A1 | 10/2003 | Bernard et al. |
| 2004/0062818 A1 | 4/2004 | Calderon |
| 2004/0137078 A1 | 7/2004 | Najafi et al. |
| 2004/0208940 A1 | 10/2004 | Selkon |
| 2005/0139808 A1 | 6/2005 | Alimi |
| 2005/0142157 A1 | 6/2005 | Alimi |
| 2005/0196462 A1 | 9/2005 | Alimi |
| 2005/0221113 A1 | 10/2005 | Bitowft et al. |
| 2006/0235350 A1 | 10/2006 | Alimi et al. |
| 2006/0241546 A1 | 10/2006 | Alimi |
| 2006/0253060 A1 | 11/2006 | Alimi |
| 2007/0173755 A1 | 7/2007 | Alimi et al. |
| 2007/0196357 A1 | 8/2007 | Alimi et al. |
| 2007/0196434 A1 | 8/2007 | Alimi et al. |
| 2007/0231247 A1 | 10/2007 | Bromberg et al. |

(Continued)

OTHER PUBLICATIONS

Bickford, Larry, The Home EyeCare First Aid Kit, 1995, The EyeCare Connection, pp. 1-5.*

(Continued)

*Primary Examiner* — Trevor Love
(74) *Attorney, Agent, or Firm* — Bingham McCutchen LLP

(57) ABSTRACT

The present invention provides methods and compositions for treating and preventing conditions characterized by infection and/or inflammation, especially of the eyes, ears, nose, and/or throat. The methods of the invention involve administering hypohalous acid to the patient, such as in the form of a composition described herein.

11 Claims, 3 Drawing Sheets

(56) References Cited

U.S. PATENT DOCUMENTS

| | | |
|---|---|---|
| 2007/0292488 A1 | 12/2007 | Bassiri et al. |
| 2007/0292489 A1 | 12/2007 | Bassiri et al. |
| 2008/0279963 A1 | 11/2008 | Najafi et al. |
| 2009/0221989 A1 | 9/2009 | Najafi et al. |
| 2010/0092399 A1 | 4/2010 | Alimi et al. |
| 2010/0106079 A1 | 4/2010 | Alimi |
| 2010/0112092 A1 | 5/2010 | Northey |
| 2010/0166809 A1 | 7/2010 | Northey et al. |
| 2011/0020474 A1 | 1/2011 | Najafi et al. |
| 2012/0164235 A1 | 6/2012 | Northey |
| 2012/0207853 A1 | 8/2012 | Alimi et al. |

OTHER PUBLICATIONS

Christensen, Eric, Gf and An Overview of OxcideTM: The Definitive Solution to Disinfection in Facility Water Distribution Systems & Equipment, 2003, pp. 1-17.*

MSDS Oxcide, Oxcide, 2005, 2 pages.*

Washington Publishers, Poison Ivy, Washington Publishers, 2005, pp. 1-5.*

Women's Heathcare Topics, Stuffy Nose During Pregnancy, 2006, pp. 1-4.*

Database Derwent on West (USPTO), London: Derwent Publications Ltd., AN 1998-537385, JP 10236961 A (Nobel Igaku Kenkyusho YG), abstract.

* cited by examiner

METHODS AND COMPOSITIONS FOR
TREATING CONDITIONS ASSOCIATED
WITH INFECTION AND/OR INFLAMMATION

This application is a National Stage of PCT/US08/51208, filed Jan. 16, 2008, which claims the benefit of U.S. Provisional Application No. 60/885,122, filed Jul. 16, 2007, each of which are hereby incorporated by reference in their entirety.

FIELD OF THE INVENTION

The present invention relates to compositions and methods for treating or preventing conditions characterized by infection and/or inflammation by administering hypohalous acid to the affected or susceptible areas. The invention is applicable to conditions affecting, for example, the eye, ear, nose, mouth, and/or throat.

BACKGROUND OF THE INVENTION

Many health conditions are characterized by infection and/or inflammation, such as various conditions of the eyes, ears, nose, and throat. While often difficult to discern underlying causes in a particular case, such conditions may be treated with, for example, topical or systemic antibiotics, antivirals, and/or anti-inflammatory agents depending on the suspected etiology. Such treatments are however limited by microbial resistance, drug toxicity, irritation, and/or hypersensitivity that may develop. Methods and compositions for broadly, effectively, and safely treating infected regions and/or inflammatory conditions of the body are needed.

For example, conjunctivitis, commonly known as pink eye, is an inflammation of the conjunctiva, the outer-most layer of the eye that covers the sclera. While many of the signs and symptoms of conjunctivitis are relatively non-specific, there are several etiologies that may be causative in a given case. The three most common causes of conjunctivitis are bacterial infection, viral infection, or an allergic reaction.

Bacterial conjunctivitis is commonly caused by *staphylococcus* and *streptococcus* bacteria, and in the case of newborns, may result from vertical transmission of *Neisseria* or *Chlamydia* from an infected mother. The symptoms and the severity of bacterial conjunctivitis depend on the bacteria involved. For example, when caused by a pyogenic bacteria, the infection may produce a stringy, opaque discharge that may cause matting of the eyelids. There may be severe crusting of the infected eye and surrounding skin. Where bacterial conjunctivitis is suspected, the condition is treated with an antibiotic effective for a broad range of bacteria. Where initial antibiotic treatment is unsuccessful, bacterial cultures can be initiated to guide treatment, although negative results are fairly common since some bacteria implicated in conjunctivitis are not easily cultured by usual laboratory culturing methods. Bacterial conjunctivitis can be quite contagious, and easily spreads from one eye to the other and from person to person. Ear infections commonly occur in children with persistent bacterial conjunctivitis.

Viral conjunctivitis may be associated with an upper respiratory tract infection, cold, or sore throat and may be caused by adenovirus. Viral conjunctivitis sometimes produces a water discharge. While the infection runs its course, the symptoms of viral conjunctivitis can be relieved with cool compresses and artificial tears. For more severe cases, topical steroid drops may be prescribed to reduce the discomfort from inflammation. These are not without side effects, especially with prolonged use.

Allergic conjunctivitis occurs more frequently among those with allergic conditions and may be caused by intolerance to substances such as cosmetics, medications or fumes. For allergic conjunctivitis, cool compresses and artificial tears sometimes relieve discomfort in mild cases. In more severe cases, non-steroidal anti-inflammatory medications and antihistamines may be prescribed. Some patients with persistent allergic eye infections may also require topical steroid drops.

Blepharitis is an inflammation of the eyelid margins, and is usually caused by an infection of *Staphylococcus aureus*. Treatment generally involves cleaning the lid and applying a topical antistaphylococcal antibiotic. Blepharitis can lead to a chalazion, or lead to a stye (hordeolum).

A chalzion is a cyst in the eyelid caused by inflammation of a blocked meibomian gland, usually on the upper eyelid. A chalazion may spawn bacterial infection. When the condition does not resolve on its own, a chalazion may be injected with corticosteroid or be surgically removed.

Hordeola include both external hordeolum, or "stye", and internal hordeolum (acute meibomianitis). Styes are lesions at the base of the eyelashes and are predominantly caused by infection of *Staphylococcus aureus*. Treatment may involve draining and topical application of an antibiotic to the lesion.

Infections may afflict the lacrimal system of the eye, such as canaliculitis and dacrocystitis. Canaliculitis can be caused by Actinomyces infection and treatment typically involves mechanical expression of the exudative or granular material from the canaliculi, combined with probing and irrigation of the nasolacrimal system with a penicillin eyedrop solution. Dacrocystitis is often due to streptococci or *Staphylococcus aureus* and is usually treated with antibiotics.

Rhinitis, an inflammation of the nasal mucous membrane, may produce nasal decongestion and rhinorrhea. Rhinitis is typically of viral origin, but may involve secondary bacterial infection. Acute rhinitis may be treated for symptoms, for example, with decongestants such as pseudoephedrine. Where bacterial superinfection is involved, antibiotics may be administered.

Rhinorrhea and nasal congestion are typically of viral or allergic origin. In certain instances, congestion is observed as an after-effect of topical decongestants (rhinitis medicamentosa). Allergic congestion and rhinorrhea are treated with antihistamines. While topical or oral decongestants (e.g., pseudoephedrine) can provide some symptomatic relief, prolonged use is not recommended.

Otitis media, inflammation of the middle ear structures, can lead to loss of equilibrium and deafness. Otitis media is generally of bacterial or viral origin. Viral infections may spawn secondary bacterial infections, including infections of *Streptococcus pneumonia, Moraxella catarrhalis*, and non-typable *Haemophilus influenzae*. Where bacterial infection is suspected, the condition may be treated with antibiotics, as well as analgesics.

External otitis is an acute or chronic inflammation of the external ear canal, and may involve bacterial (e.g., *Pseudomonas aeruginosa, Proteus vulgaris*, and *Staphylococcus aureus*) or fungal (e.g., *Aspergillus* and *Candida*) infection. External otitis may be treated with, for example, antibiotics and corticosteroids.

Pharyngitis (sore throat) is characterized by pain and swelling in the posterior pharynx. Pharyngitis is commonly caused by bacterial (e.g., Streptococcal) or viral infection, and may be treated with topical anesthetics.

Stomatitis is a painful ulcer or inflammation of the oral mucosa. Stomatitis may be caused, for example, by infection (bacterial, viral, or fungal), chemical irritant, or allergic reaction, and may be common for patients having Xerostomia. Some common infectious agents include herpes simplex virus, varicella zoster, Epstein-Barr virus, influenza, cytomegalovirus, *Gonorrhea*, and *Candida*. Treatments for stomatitis include anesthetics, corticosteroids, antihistamines, and/or antibiotics.

It is an object of the invention to provide a broadly effective and safe treatment for conditions characterized by infection (bacterial, viral, or fungal), and/or inflammation (including acute and chronic inflammation, as well as delayed-type and immediate-type hypersensitivity), so as to avoid development of bacterial resistance to antibiotics, and so as to avoid toxicity, irritation, and/or hypersensitivity that may occur with conventional agents.

SUMMARY OF THE INVENTION

In one aspect, the present invention provides a method for treating a condition involving infection and/or inflammation, including acute and chronic inflammation, as well as delayed-type and immediate-type hypersensitivity. Such conditions include ocular conditions, such as those affecting the conjunctiva, uvea, eye lids, oil glands, and lacrimal ducts, such as: bacterial, viral, or allergic conjunctivitis, uveitis, blepharitis, external and internal hordeolum, canaliculitis, dacrocystitis, and chalazions. Such conditions also include various conditions affecting the ear (including the inner ear, middle ear, ear canal, and ear drum), nose, mouth and throat, including rhinitis, sinusitis, rhinorrhea, otitis media, external otitis, myringitis, pharyngitis, and stomatitis.

The invention involves administering a hypohalous acid, such as HOCl, to the affected area as described herein. The invention provides a broadly effective method for cleansing and treating the inflamed and/or infected regions, and in a manner relatively independent of the etiology of the inflammation or infection, and in a manner that is free of toxicity and hypersensitivity. The method of the invention is useful as an alternative or adjunct therapy to conventional antibiotics, antivirals, decongestants, antihistamines, and steroid treatments, or as an alternative to therapy using a combination of conventional medicaments.

In a second aspect, the present invention provides a composition containing hypohalous acid for treating inflamed and/or infected regions of the eye, ear, nose (including sinuses), or throat. In an exemplary embodiment, the composition is an electrolyzed saline solution comprising hypohalous acid, or consisting essentially of a hypohalous acid, as an active agent, and a pharmaceutically acceptable carrier. The electrolyzed solution may have a pH of from about 4 to about 7 and an available free chlorine (AFC) content of from about 20 to about 1000 parts per million (ppm). The composition of the invention is broadly effective for cleansing, disinfecting, and/or reducing inflammation of the eyes, ears, nose, mouth, and/or throat. The composition of the invention is useful as an alternative or adjunct to conventional treatments, and is particularly suitable for prolonged use and hygiene, especially for individuals prone to such infections and/or inflammatory conditions, or individuals that typically experience hypersensitivity with other treatments.

DETAILED DESCRIPTION OF THE INVENTION

Figure 1:
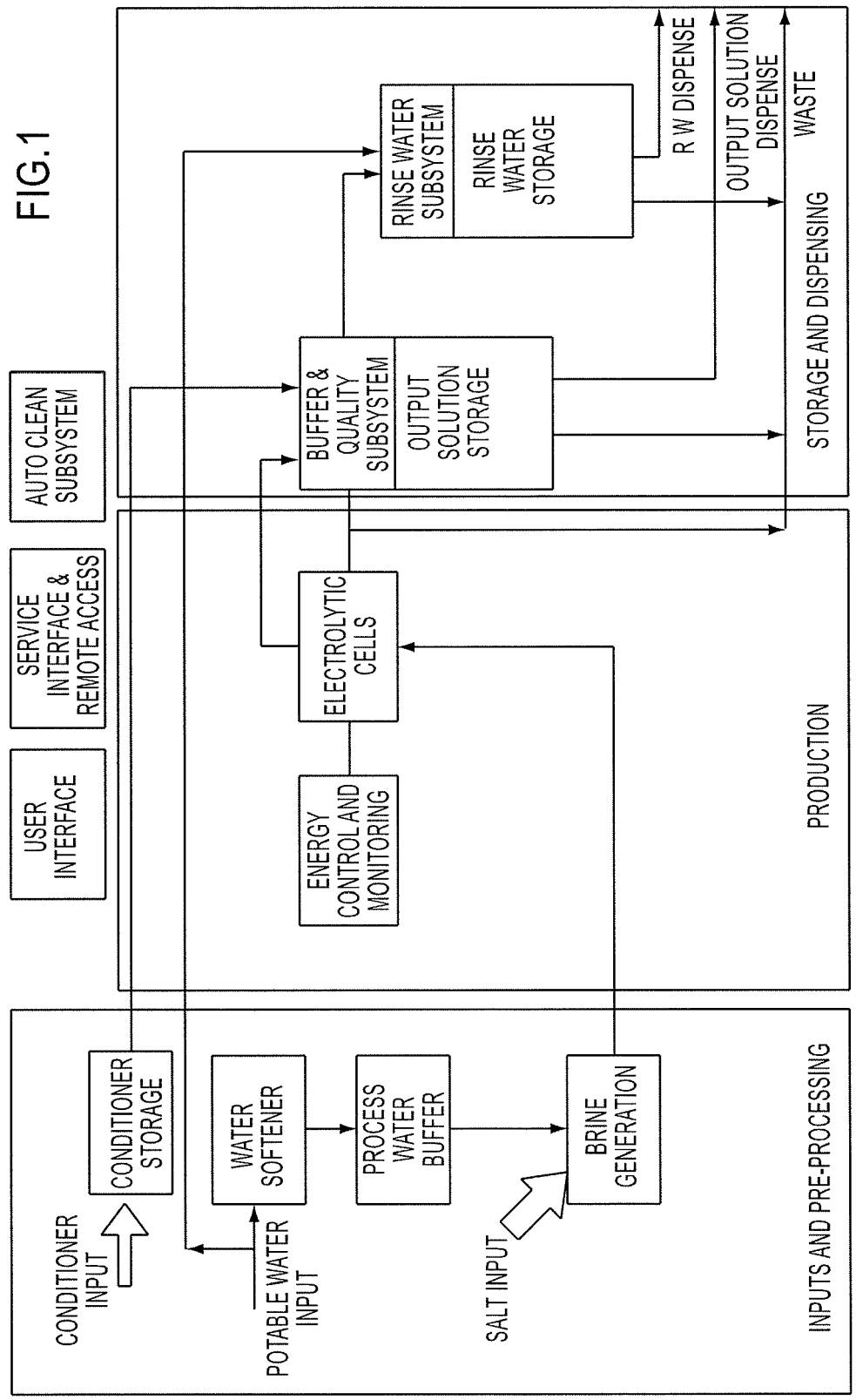
FIG. 1 is a schematic outline of the main processing stages for producing an electrolyzed saline solution in accordance with certain embodiments of the present invention.

The present invention provides compositions and methods for treating a condition characterized by infection and/or inflammation, such as conditions of the eyes, ears, nose, mouth, and/or throat, by administering a hypohalous acid, such as HOCl, to the affected area as described herein.

Hypohalous Acid, Solutions, and Compositions

Hypochlorous acid (HOCl) is an oxidant and biocide that is produced by the human body's natural immune system. HOCl is generated as the final step of the Oxidative Burst Pathway, with large quantities of HOCl being released into phagocytic vesicles to destroy invading microorganisms. It is considered, without wishing to be bound by any theory, that hypochlorous acid exerts a biocidal effect by attacking the surface and plasma membrane proteins, impairing transport of solutes and the salt balance of bacterial cells (Pieterson et al, Water SA, 22(1): 43-48 (1996)). In accordance with the present invention, exogenous hypohalous acid is administered for treating or preventing conditions characterized by infection and/or inflammation. The compositions of the invention are non-irritating and non-sensitizing to the skin, non-irritating to the eyes, not harmful if swallowed, show no evidence of mutagenic activity, and are safe for routine or prolonged use. An added advantage is that there is no resistance or tolerance developed by the microorganisms, as occurs with the use of conventional antibiotics, and there is generally no hypersensitivity as occurs with some agents conventionally administered to treat microbial infections and inflammatory conditions.

The hypohalous acid solution may be generated by electrolysis of salt, such as saline (NaCl), and may contain a mixture of oxidizing species such as predominantly hypochlorous acid (HOCl) and sodium hypochlorite. Hypochlorous acid and hypochlorite are in equilibrium and the position of the equilibrium is determined solely by the pH, which may be controlled by the electrochemical generator. The hypohalous acid solution may have a pH of from about 4 to about 7, but in certain embodiments has a pH of from about 5 to about 7, or from about 5.0 to about 6.5, or from about 5.4 to about 5.8. For example, the hypohalous acid solution may have a pH of about 5.4. The pH of the solution can be controlled, for example, by modulating the chemical properties of the solution, or (where an electrolyzed solution is used as the source of hypohalous acid) the hydraulic regime within the electrochemical cell system, the applied electric current, or the recirculation of the catholyte produced by the electrochemical cell.

In certain embodiments, the electrolyzed solution consists of essentially hypohalous acid as the active agent (e.g., HOCl), but in certain other embodiments may contain, or may also contain, other oxidizing or radical producing species such as a hypohalite (e.g., hypochlorite), hydroxide, $H_2O_2$ and $O_3$. These species may provide additional biocidal activity, and may have additional benefits for clearing bacterial debris, biofilm, or discharge, such as where the hypohalous acid solution is used for treating ear infections, bacterial conjunctivitis or for cleaning or storing contact lenses. In certain embodiments, the hypohalous acid solution contains at least 80% hypohalous acid relative to the total concentration of hypohalous acid, hypohalite, and $Cl_2$ (as 100%). The hypohalous acid may have, however, at least 90%, at least 95%, or at least 98% hypohalous acid. Such embodiments may allow for higher levels of active chlorine to be administered, while avoiding any irritation as a result of the solution.

The hypohalous acid solution, such as an HOCl solution, prepared by electrolysis of salt or saline, contains an available free chlorine (AFC) content of from about 5 to about 1000 parts per million. The desired AFC content may be controlled by an apparatus as described herein. In some embodiments, the solution of the invention has an AFC content of less than about 250 parts per million. For example, the solution may have an AFC content of from about 20 to about 200 ppm, such as from about 100 to about 200 ppm, or of from about 50 to about 100 ppm, or from about 20 to about 50 ppm. Such solutions may be particularly suited for routine use and/or prophylactic care, including routine cleansing and hygiene. In certain other embodiments, the solution has an AFC content of greater than about 250 ppm. For example, the solution may have an AFC content of from about 250 to about 600 ppm, or from about 250 to about 400 ppm, or from about 400 to about 500 ppm, or from about 500 to about 600 ppm. While such solutions are potent biocides, and may help reduce and control inflammation, including immediate-type hypersensitivity reactions, such solutions are not generally irritating to the skin, eye, nasal mucosa, and ear, and are not harmful to contact lenses.

The electrolyzed solution of the invention may also contain from about 0.2 to 2.0% w/v salt, such as NaCl. In some embodiments, the invention contains 0.4 to 1.5% w/v salt, or may be a normal saline solution (0.9% w/v NaCl). In some embodiments, the solution is isotonic with physiological fluids, such blood, saliva or tears. While the hypohalous solution may be administered at room temperature, the solution may alternatively be heated, for example, to body temperature or about body temperature, or above body temperature to help drain fluids from the site of infection as well as loosen oils that spawn infection. In certain embodiments, the hypohalous acid is administered at below body temperature. Such embodiments may be particularly suited to control acute inflammation.

The hypohalous acid may be prepared by electrolysis of one or more halide salts, including Cl, Br, I, F, and At. Thus, the hypohalous acid may include one or a mixture of HOCl, HOBr, HOI, HOF, and HOAt. In certain embodiments, the electrolyzed solution is generated using a mixture of physiologically balanced salts, as disclosed in U.S. Pat. No. 6,426,066, which is hereby incorporated by reference in its entirety. Such salts may include sodium halides (e.g., NaCl), potassium halides (e.g., KCl) and magnesium halides (e.g., $MgCl_2$).

While the composition of the invention may be formulated as a liquid, such as an eye drop, eye wash, wash for contact lenses, gargle, nasal or throat spray, or ear drop, the composition may alternatively take the form of a cream, gel, and/or foam for application to the skin surrounding the eye. Such formulations may be prepared using convention additives known in the art and/or as described herein. In embodiments employing creams, gels, and/or foams, the solution is better contained around the site of infection or inflammation by limiting run-off. Convenient applicators for creams, foams, and the like are known, and may be used in accordance with the present invention. Alternatively still, the composition of the invention may be formulated so as to be delivered by aerosol, mist, or steam.

The electrolyzed solution may have an oxidation reduction potential (redox) of greater than about +650 mV, greater than about +950 mV, such as about +1000 mV. A high redox potential allows for the quick and efficient destruction of microbes (bacteria, viruses, fungi and spores). In certain embodiments of the invention, the hypohalous acid solution has a biocide rate (D Value) of approximately 1 log reduction of *Bacillus subtilis* spores in less than 1 minute with a 9:1 electrolyzed solution: innoculum mix. In some embodiments, the solution has a biocide rate of as low as 3.4 seconds. Generally, the hypohalous acid is effective on a broad spectrum of bacterial, fungal, and viral pathogens.

In certain embodiments of the present invention, the hypohalous acid is formulated or administered in combination with another therapeutic agent. Non-limiting examples of therapeutic agents include anti-microbial agents such as antibiotics, anti-inflammatory agents, anti-histamines, analgesics, anti-oxidants such as vitamins, and moisturizing agents. For example, the hypohalous acid may be formulated or administered with bacitracin, neomycin, neosporin, framycetin, fusidic acid, corticosteroid, chloramphenicol, gentamicin, tobramycin, ceftriaxone, sulfacetamide, erythromycin, gentamicin, ciprofloxacin, ofloxacin, cefoxitin, cefotaxime, spectinomycin, tetracycline, doxycycline, azithromycin, and/or acyclovir.

The composition may comprise a pharmaceutically acceptable carrier. Non-limiting examples of suitable carriers include polyvinyl alcohol, povidone, hydroxypropyl methyl cellulose, poloxamers, carboxymethyl cellulose, hydroxyethyl cellulose, and purified water. The compositions of the present invention may also include various other ingredients, such as tonicity agents, buffers, surfactants, co-solvents, viscosity building agents, preservatives, and other therapeutic agents.

Regarding tonicity agents, such agents may be employed to adjust the tonicity of a composition, for example, in the case of an ophthalmic composition, to the tonicity of natural tears. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added and the type of composition. In general, however, the compositions will have a tonicity agent in an amount sufficient to cause the final composition to have an acceptable osmolality. For example, for an ophthalmic composition, the composition generally about 150 to 450 mOsm, preferably 250 to 350 mOsm.

Regarding buffers, an appropriate buffer system (such as, for example, sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 4-7 or a range as described herein.

Regarding a surfactant, various surfactants useful in conventional formulations may be employed. Exemplary surfactants include Cremophor® EL, polyoxyl 20 ceto stearyl ether, polyoxyl 40 hydrogenated castor oil, polyoxyl 23 lauryl ether and poloxamer 407.

Regarding viscosity building agents, such agents may be added to compositions of embodiments of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. For example, the composition may exhibit a viscosity of 1 to 400 centipoises ("cps").

Regarding preservatives, suitable preservatives include benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. In addition, the composition of the present invention may include antimicrobial agents such as antibacterials to provide safety and efficacy for storage stability. The amount of antibacterial can be within the range of from about 0.004% to about 0.5% by weight/volume of the composition. A suitable antibacterial would include, for example, from about 0.004% to about 0.02% by weight/volume of benzalkonium chloride, from about 0.25% to about 0.5% of chlorobutanol, about 0.1% of thimerosal, about 0.05% methylbaraben, about 0.01% propylbaraben, and sodium chloride in an amount sufficient to make an isotonic solution. The composition can also include other therapeutic agents such as anti-inflammatory agents, antihistamines, decongestants, antibiotics, and/or moisturizing agents known in the art.

Ocular Conditions

In certain embodiments, the present invention relates to treating an ocular condition, especially an ocular condition(s) originating from an infection and/or inflammatory condition. The ocular condition may affect any portion of the eye or surrounding areas, such as the conjunctiva, uvea, eyelid, oil glands, and lacrimal ducts. Exemplary ocular conditions include: red eye; dry eye (including dry eye syndrome); conjunctivitis of bacterial, viral, or allergic origin; uveitis, blepharitis; external or internal hordeolum; canaliculitis; dacrocystitis; and chalazions. The ocular condition may be present in a human or animal patient. Exemplary animal patients include mammals such as dogs, cats, horses, lamb, cattle, goats, pigs, and guinea pigs. The present invention further contemplates preventive care for such ocular conditions.

The invention includes the treatment and prevention of ocular infections caused by a variety of pathogens, such as, for example, a bacterial agent, a viral agent, a parasitic agent, and/or a fungal agent. Non-limiting examples of bacterial agents include *Streptococcus* spp. (e.g. *pneumoniae*), *Staphylococcus* spp. (e.g., *aureus*), *Haemophilus* spp. (e.g., *influenzae*), *Pseudomonas* spp. (e.g., *aeruginosa*), *Chlamydia* spp. (e.g., *trachomatis, psittaci, pecorum*), *Neisseria* spp. (e.g. *gonorrhoeae*), and *Actinomyces* species. Non-limiting examples of viral agents include adenovirus, respiratory syncytial virus (RSV), influenza (including parainfluenza), coxackie virus, rhinovirus, coronavirus, and herpes simplex virus. Non-limiting examples of fungal agents include *Candida* species, *Fusariu* species, and *Aspergillus* species. A non-limiting example of a parasitic agent is an eyeworm. Certain bacterial agents may be more common in certain patient subpopulations. For example, different strains of *Chlamydia psittaci* and *Chlamydia pecorum* cause significant eye infection in cats, lambs, goats, and guinea pigs. These infections are occasionally transmitted to humans. Further, eyeworms are common parasites of horses and cattle, goats, pigs, dogs and cats.

These microbial agents may be involved in various ocular infections including blepharitis; hordeola, such as external hordeolum and internal hordeolum; conjunctivitis, such as viral conjunctivitis or bacterial conjunctivitis, conjunctivitis in newborns (opthalmia neonatorum) due to *Chlamydia trachomatis* or *Neisseria gonorrhoeae*, chlamydial disease in adults such as inclusion conjunctivitis and trachoma, or gonococcal conjunctivitis in adults; iridocyclitis and panopthalmitis caused by *Bacillus subtilis*; lacrimal system infections such as canaliculitis and dacrocystitis; keratitis, such as viral keratitis (herpes simplex virus), bacterial keratitis and fungal keratitis (e.g., *Fusarium*), including among soft contact lens wearers; toxoplasmosis, including in dogs and cats; feline herpes virus, which is a common cause of eye and upper respiratory infections in cats; uveitis, including in large animals, such as cattle, caused by *Listeria*; and eye infections caused by avian flu or other eye conditions and infections secondary to other medical conditions.

In certain embodiments of the invention, the ocular condition involves a bacterial infection that is antibiotic resistant. For example, the bacterial infection may be resistant to antibiotics commonly employed to combat eye infections either topically or systemically, such as sulfacetamide, erythromycin, gentamicin, ciprofloxacin, ofloxacin, cefoxitin, ceftriaxone, cefotaxime, spectinomycin, tetracycline, doxycycline, azithromycin, or bacitracin. In these and other embodiments, the bacterial invention may be resistant to beta-lactam antibiotics or fluoroquinolones. For example, the infection may involve methicillin-resistant *Staphylococcus aureus* (MRSA), for which the present invention is effective.

In certain embodiments, the ocular condition involves a viral infection, which may further include a secondary bacterial infection, such that conventional antibiotic treatment is necessarily insufficient.

In certain embodiments, the ocular condition may be a bacterial infection that produces a discharge that hinders vision and/or eye function, such as bacterial conjunctivitis. In these embodiments, the invention provides the benefit of effectively cleaning sticky discharge, biofilm, or debris from the eye in a manner that reduces the risk of spreading the infection to an unaffected eye or another individual. Where the condition involves biofilm, the hypohalous acid deactivates the polymatrix material of the biofilm to facilitate removal (cleansing), and disinfection. Hypohalous acid contact with biofilm formation dissolves the protective polysaccharaide matrix of the biofilm aiding in the effective removal of pathogens and debris.

In certain embodiments, the ocular condition involves an inflammatory disorder or hypersensitivity reaction (including types I, II, III, and/or IV). For example, the ocular condition may involve an immediate-type hypersensitivity reaction such as allergic conjunctivitis. In other embodiments, the condition may result from a blocked gland or chronic inflammatory condition, including styes and chalazions, which may also develop an acute bacterial infection. Such conditions may be recurring or may be difficult to completely clear. Other inflammatory ocular conditions that may or may not involve microbial infection, include uveitis.

In certain embodiments, the ocular condition is prevention of infection and/or inflammation resulting from an eye surgery.

Modes of Treatment For Ocular Conditions

Treating an ocular condition in accordance with the present invention generally involves alleviating the cause or symptoms of the condition, and can include: reducing inflammation or hypersensitivity in the eye or surrounding area; reducing irritation in the eye or surrounding area; reducing redness in the eye; reducing discharge from the eye; improving vision from the eye; clearing a microbial infection; preventing, or reducing the spread of a microbial infection, including the spread of infection from the infected eye to an uninfected eye; and moisturizing or reducing dryness of the eye. These can be measured or determined by comparing the patient's condition prior to and after treatment with hypohalous acid in accordance with the present invention. Alternatively, treatment can be determined relative to a patient having the same or similar condition who has not been treated with the hypohalous acid in accordance with the present invention. In certain embodiments, the administration of hypohalous acid treats both an infection and inflammation, such as acute or chronic inflammation, associated with an ocular condition.

In certain other embodiments, the hypohalous acid is administered prophylacticly, especially where eye infections are likely to occur or be transmitted among persons. Thus, in this embodiment, the invention involves administering the hypohalous acid before an infection develops. Such prophylactic care might include routine cleaning of the eyes and surrounding areas, such as the eyelids, with the hypohalous acid, or routine rinsing of contact lenses by applying the hypohalous acid to the contact lenses to decontaminate and clear debris and biofilm. Such embodiments can result in the prevention of an ocular infection, can prevent the worsening of an existing ocular infection caused by contaminated lenses, or can prevent irritation of the eyes caused by bacterial biofilm. In other embodiments, the invention involves administering hypohalous acid to the environment via fogging, misting, or humidifying, to prevent the transfer of pathogens from air droplets into the eyes of susceptible individuals.

In certain embodiments of the invention, the ocular condition involves a bacterial infection that is antibiotic resistant. For example, the bacterial infection may be resistant to antibiotics commonly employed to combat eye infections either topically or systemically, such as sulfacetamide, erythromycin, gentamicin, ciprofloxacin, ofloxacin, cefoxitin, ceftriaxone, cefotaxime, spectinomycin, tetracycline, doxycycline, azithromycin, or bacitracin. In these and other embodiments, the bacterial invention may be resistant to beta-lactam antibiotics or fluoroquinolones. In these embodiments, the hypohalous acid of the invention may be administered after unsuccessful topical or systemic antibiotic treatment. For example, where the invention reoccurs or is generally unaffected by antibiotic treatment, hypohalous acid may be administered to the affected regions has discussed herein, without further investigation as to the causative agent where not practical. In still other embodiments, the hypohalous acid may be administered to the affected regions in place of antibiotic treatment, thus making antibiotic treatment unnecessary. For example, administering hypohalous acid in accordance with the present invention may be used as an alternative to administration of a beta-lactam or fluoroquinolone antibiotic, thereby avoiding the hypersensitivity reactions common with such drugs. This embodiment is particularly advantageous where antibiotic resistance has already been developed by the microorganism, the hypohalous acid being an alternative to potential "last lines of defense" with antibiotic treatment, since resistance will not be developed to the hypohalous acid, and no further resistance to conventional antibiotics will then be cultivated.

In certain embodiments, the invention is a superinfection, including both viral and bacterial etiology. In such embodiments, the hypohalous acid may be administered in place of other agents or combination therapies, to treat and or help clear the various microbial pathogens.

The hypohalous acid may also be used as an adjunct cleanser along with antibiotic or steroidal treatment to provide synergistic disinfecting and/or anti-inflammatory effects. For example, when used in conjunction with an antibiotic, the treatment provides a potent antimicrobial effect, while avoiding or limiting the development of antibiotic resistance. This aspect of the infection is particularly useful where the infection is chronic or recurring, since continued or repeated antibiotic treatment is generally not accepted.

In certain embodiments, the ocular condition may be a bacterial infection that produces a discharge that hinders vision and/or eye function, such as bacterial conjunctivitis. In these embodiments, cleaning the eye and the surrounding areas with the hypohalous acid of the invention provides the benefit of effectively cleaning debris, biofilm, and/or discharge from the eye in a manner that reduces the risk of spreading the infection to an unaffected eye or another individual.

In certain embodiments, the ocular condition may result from an acute or chronic inflammatory condition, which may develop an acute infection. In these embodiments, the hypohalous acid is administered to treat both the infection and the underlying inflammation. Thus, the hypohalous acid may be administered instead of steroidal drops or systemic steroidal medications, or antibiotics, thereby avoiding the potential adverse reactions of such treatments. In certain other embodiments, the hypohalous acid is used to clean the region during the duration of steroidal and/or antibiotic treatment. In one embodiment, hypohalous acid is administered to the eye of a patient inflicted with uveitis, during the duration of steroid treatment. For example, the hypohalous acid may be used in conjunction with glucocorticoid steroids, either as topical eye drops (such as betamethasone, dexamethasone or prednisolone) or oral therapy with prednisolone tablets. Likewise, when the condition has an allergic origin, such as allergic conjunctivitis, the hypohalous acid may be used alongside an antihistamine to more effectively inhibit release of inflammatory mediators from mast cells.

In certain embodiments of the present invention, the hypohalous acid solution is administered with treatment using a warm compress, especially where the condition is blepharitis, an external hordeolum, an internal nordeolum, or a chalazion. In these embodiments, the hypohalous acid may be used for routine cleansing of the affected area for the duration of the treatment, and after treatment to avoid recurrence of the condition.

In certain embodiments, the hypohalous acid solution may be administered to two or more sites in the ocular system of a patient. For example, the hypohalous acid may be administered as drops to the eye or eye wash, and as a cleanser for the eye lids and/or eyelid margins.

In another embodiment, the hypohalous acid treatment is followed by treatment with an antioxidant, such as a vitamin.

The hypohalous acid and compositions of the present invention may be administered in any appropriate dosage form such as a liquid, aerosol, gas, or semi-solid including a solution, suspension, viscous or semi-viscous gel, ointment, cream, or other types of compositions. Preferably, the solution is administered topically either dropwise into the eye or to the tissue surrounding the eye. The solution or composition comprising the solution can also be formulated into a sterile solution for administration by intracameral injection into the anterior chamber of the eye or directly into the trabecular meshwork of the eye. The doses used for the above described purposes can be determined by a physician or other qualified medical personnel and can depend, for example, on the type of ocular condition, the frequency of administration (i.e. for chronic or acute use), the severity of the condition, the age and overall health of the patient, the dosage form of the hypohalous acid, and other factors. For example, in one non-limiting embodiment, 1 to 2 drops of an electrolyzed saline solution is administered 1 to 10 times per day. In another embodiment, the solution is administered 1 to 4 times per day.

For chronic or routine use, one to two drops of the solution can be administered once or twice daily, similar to artificial tears. One non-limiting example of a chronic indication is using hypohalous acid drops for dry eyes or for rinsing or storing contact lenses. The hypohalous acid drops may be used to sooth/bath eyes from everyday wear and tear, such as, for example, from computer screen glare, dust and other environmental contaminants, exposure to air-conditioning, general dryness and other causes. The AFC concentration of the hypohalous acid solution may vary depending on whether the solution is used chronically or acutely. For example, for chronic use, the AFC concentration may be on relatively low. For example, in certain embodiments, the AFC concentration is from about 5 to about 100 ppm, such as from about 5 to about 20 ppm. For acute use, such as an acute microbial infection, the AFC concentration should be sufficient to kill or reduce bacteria associated with the infection. Thus, for acute uses, the AFC concentration may be relatively high. For example, in certain embodiments, the AFC concentration is from about 200 to about 650 ppm. In certain other embodiments, the AFC concentration is from about 200 to about 400 ppm.

Conditions of the Ears, Nose, and Throat

The present invention provides treatments as well as preventive care for conditions characterized by infection and/or inflammation of the ears (including the outer ear, middle ear, and inner ear), nose (including sinus care), mouth, and throat. Exemplary conditions include: rhinitis, rhinorrhea, nasal congestion, otitis media, external otitis, pharyngitis, and stomatitis, and may be present in a human or animal patient. Exemplary animal patients include mammals such as dogs, cats, horses, lamb, cattle, goats, pigs, and guinea pigs. The present invention further provides preventive care for such conditions, especially where such conditions are recurring, such as recurring ear infection, sinus infection, sore throat, or mouth ulcer.

In these embodiments, the invention includes the treatment and prevention of infections caused by a variety of pathogens, such as, for example, a bacterial agent, a viral agent, a parasitic agent, and/or a fungal agent. Non-limiting examples of bacterial agents include *Streptococcus* spp. (e.g. *pneumoniae*), *Staphylococcus* spp. (e.g., *aureus* including MRSA), *Haemophilus* spp. (e.g., *influenzae*), *Moraxella* spp., *Pseudomonas* spp. (e.g., *aeuruginosa*), *Chlamydia* spp. (e.g., *trachomatis, psittaci, pecorum*), *Neisseria* spp. (e.g. *meningiditis*), *Mycobacterium*, and *Actinomyces* species. Non-limiting examples of viral agents include adenovirus, respiratory syncytial virus (RSV), influenza (including parainfluenza and avian flu), coxackie virus, rhinovirus, coronavirus, varicella zoster, and herpes simplex virus. Non-limiting examples of fungal agents include *Candida* species, *Fusariu* species, and *Aspergillus* species.

In certain embodiments of the invention, the condition of the ear, nose, mouth, and/or throat involves a bacterial infection that is antibiotic resistant. For example, the bacterial infection may be resistant to antibiotics commonly employed to combat such infections either topically or systemically, such as sulfacetamide, erythromycin, gentamicin, ciprofloxacin, ofloxacin, cefoxitin, ceftriaxone, cefotaxime, spectinomycin, tetracycline, doxycycline, azithromycin, or bacitracin. In these and other embodiments, the bacterial invention may be resistant to beta-lactam antibiotics or fluoroquinolones. For example, the infection may involve methicillin-resistant *Staphylococcus aureus* (MRSA), for which the present invention is effective. Further, the invention may help control the presence and/or spread of MRSA in and from colonized individuals, that is, where no obvious infection is present. Thus, in some embodiments, the hypohalous acid is employed after antibiotic treatment to kill resistant pathogens, despite no remaining signs of infection.

In certain embodiments, the condition involves a viral infection with secondary bacterial infection (which may be antibiotic resistant), such that conventional antibiotic treatment is necessarily insufficient. For example, the condition may be a sinus infection or ear infection of viral origin, which has developed a bacterial superinfection. Unlike convention antibiotics, the invention has benefit in controlling and clearing both the viral and bacterial components of the infection.

In certain embodiments, the condition may involve a bacterial infection that produces a discharge, for example, external otitis or otorrhea. In these embodiments, the hypohalous acid effectively cleans discharge, biofilm, or debris from the ear in a manner that reduces the risk of spreading infection.

In certain embodiments, the condition involves an inflammatory disorder or hypersensitivity reaction (including types I, II, III, and/or IV). For example, the condition may involve an immediate-type hypersensitivity reaction such as allergic rhinitis or sinusitis. In other embodiments, the condition may result from a chronic inflammatory condition, which may also develop an acute bacterial infection. Such conditions may be recurring or may be difficult to completely clear.

Modes of Treating Ear, Nose, Mouth, and Throat Conditions

Treating a condition of the ear, nose, mouth, and/or throat in accordance with the present invention generally involves alleviating the cause or symptoms of the condition, and can include: reducing inflammation or hypersensitivity; reducing irritation; reducing discharge; clearing a microbial infection; preventing, or reducing the spread of a microbial infection. These can be measured or determined by comparing the patient's condition prior to and after treatment with hypohalous acid in accordance with the present invention. Alternatively, treatment can be determined relative to a patient having the same or similar condition who has not been treated with the hypohalous acid in accordance with the present invention. In certain embodiments, the administration of hypohalous acid treats both an infection and inflammation, such as acute or chronic inflammation.

In certain other embodiments, the hypohalous acid is administered prophylacticly, especially where infections are likely to occur or be transmitted among persons. Thus, in this embodiment, the invention involves administering the hypohalous acid before an infection develops. Such prophylactic care might include routine cleaning of the ear, mouth, throat, nose, or sinuses, with the hypohalous acid. Such embodiments can result in the prevention of an infection, can prevent the worsening of an existing infection, or can prevent irritation caused by bacterial biofilm. In other embodiments, the invention involves administering hypohalous acid to the environment via fogging, misting, or humidifying, to prevent the transfer of pathogens from air droplets into the ear, nasal passages, and oral cavity of susceptible individuals.

In certain embodiments of the invention, the condition involves a bacterial infection that is antibiotic resistant. For example, the bacterial infection may be resistant to antibiotics commonly employed to combat such infections either topically or systemically, such as sulfacetamide, erythromycin, gentamicin, ciprofloxacin, ofloxacin, cefoxitin, ceftriaxone, cefotaxime, spectinomycin, tetracycline, doxycycline, azithromycin, or bacitracin. In these and other embodiments, the bacterial invention may be resistant to beta-lactam antibiotics or fluoroquinolones. In these embodiments, the hypohalous acid of the invention may be administered after unsuccessful topical or systemic antibiotic treatment. For example, where the invention reoccurs or is generally unaffected by antibiotic treatment, hypohalous acid may be administered to the affected regions has discussed herein, without further investigation as to the causative agent where not practical. In still other embodiments, the hypohalous acid may be administered to the affected regions in place of antibiotic treatment, thus making antibiotic treatment unnecessary. For example, administering hypohalous acid in accordance with the present invention may be used as an alternative to administration of a beta-lactam or fluoroquinolone antibiotic, thereby avoiding the hypersensitivity reactions common with such drugs. This embodiment is particularly advantageous where antibiotic resistance has already been developed by the microorganism, the hypohalous acid being an alternative to potential "last lines of defense" with antibiotic treatment, since resistance will not be developed to the hypohalous acid, and no further resistance to conventional antibiotics will then be cultivated.

In certain embodiments, the invention is a superinfection, including of both viral and bacterial etiology. In such embodiments, the hypohalous acid may be administered in place of other agents or combination therapies, to treat and or help clear the various microbial pathogens.

The hypohalous acid may also be used as an adjunct cleanser along with antibiotic or steroidal treatment to provide synergistic disinfecting and/or anti-inflammatory effects. For example, when used in conjunction with an antibiotic, the treatment provides a potent antimicrobial effect, while avoiding or limiting the development of antibiotic resistance. This aspect of the infection is particularly useful where the infection is chronic or recurring, since continued or repeated antibiotic treatment is generally not accepted.

In certain embodiments, the condition may be a bacterial infection that produces a discharge, such as an ear or sinus infection. In these embodiments, cleaning the middle ear, ear canal, or sinuses, for example, with the hypohalous acid of the invention provides the benefit of effectively cleaning wax, debris, biofilm, and/or discharge in a manner that reduces the risk of spreading the infection to another individual. Where the condition involves biofilm, the hypohalous acid deactivates the polymatrix material of the biofilm to facilitate removal (cleansing), and disinfection. Hypohalous acid contact with biofilm formation dissolves the protective polysaccharaide matrix of the biofilm aiding in the effective removal of pathogens and debris.

In certain embodiments, the condition may result from an acute or chronic inflammatory condition, which may develop an acute infection. In these embodiments, the hypohalous acid is administered to treat both the infection and the underlying inflammation. Thus, the hypohalous acid may be administered instead of steroidal drops or systemic steroidal medications, or antibiotics, thereby avoiding the potential adverse reactions of such treatments. In certain other embodiments, the hypohalous acid is used to clean the region during the duration of steroidal and/or antibiotic treatment. In one embodiment, hypohalous acid is administered to the nasal passages and/or sinuses of an allergic patient, during the duration of steroid treatment. For example, the hypohalous acid may be used in conjunction with steroid treatment, or alongside an antihistamine to more effectively inhibit release of inflammatory mediators from mast cells.

The hypohalous acid and compositions of the present invention may be administered in any appropriate dosage form such as a liquid, aerosol, or semi-solid including a solution, suspension, gas, viscous or semi-viscous gel, ointment, cream, or other types of compositions. Such compositions include nasal sprays, throat sprays, and mouth wash. The doses used for the above described purposes can be determined by a physician or other qualified medical personnel and can depend, for example, on the type of condition, the frequency of administration (i.e. for chronic or acute use), the severity of the condition, the age and overall health of the patient, the dosage form of the hypohalous acid, and other factors. For example, in one non-limiting embodiment, 1 to 2 drops of the hypohalous acid solution is administered 1 to 10 times per day. In another embodiment, the solution is administered 1 to 4 times per day.

For chronic or routine use, one to two drops of the solution can be administered once or twice daily. The AFC concentration of the hypohalous acid solution may vary depending on whether the solution is used chronically or acutely. For example, for chronic use, the AFC concentration may be on the lower end of a range from 5 to 1000. For example, in certain embodiments, the AFC concentration is from about 5 to about 100 ppm, such as from about 5 to about 20 ppm. For acute use, such as an acute microbial infection, the AFC concentration should be sufficient to kill or reduce bacteria associated with the infection. The AFC concentration is preferably on the higher end of a range from 5 to 1000 ppm. For example, in certain embodiments, the AFC concentration is from about 200 to about 650 ppm. In certain other embodiments, the AFC concentration is from about 200 to about 400 ppm.

For patients afflicted with a sinus infection and/or allergic condition, the present invention provides for administration of the hypohalous acid as described herein to the nose and/or sinus cavity. In these embodiments, the invention provides a broadly effective and safe treatment for sinus conditions characterized by infection and/or inflammation (including immediate-type hypersensitivity), so as to avoid development of bacterial resistance to antibiotics, and so as to avoid toxicity, adverse effects, irritation, and/or hypersensitivity that may occur with other agents including antihistamines. In these embodiments, the hypohalous acid as described herein may be administered to the nose or sinuses of an affected patient as an alternative or adjunct therapy to antibiotics and/or antihistamines, or other convention treatment, depending on the suspected etiology of the condition. In accordance with these embodiments, the hypohalous acid may be administered as a nasal spray using conventional formulation as described in U.S. Pat. No. 6,565,832, for example, which is hereby incorporated by reference in its entirety.

In another embodiment, the hypohalous acid treatment is followed by treatment with an antioxidant, such as a vitamin.
Production of Hypohalous Acid and Compositions of the Invention The hypohalous acid solution for use in the methods and compositions of the present invention may be prepared by electrolysis of a salt solution. Exemplary methods and apparatuses for preparing electrolyzed solutions are disclosed in US published patent application no. 2004/0060815, which is hereby incorporated by reference in its entirety.

In one embodiment, a salt solution (electrolyte) may be pre-packaged and provided for preparing the hypohalous acid solution on demand by electrolysis. In other embodiments, the electrolyte may be provided in dry form, and mixed with de-ionized and/or softened water to prepare the hypohalous acid on demand.

FIG. 1 provides a schematic outline of the main processing stages of a non-limiting, exemplary method for producing an electrolyzed saline solution. Such a method involves an input and pre-processing stage; a production stage; and a storage and dispensing stage. In the input and pre-processing stage, water can be passed through a water softener zone where excess magnesium and calcium ions are removed. The resultant softened water can be passed as process water to a brine generation zone where a salt (e.g., a halide salt such as NaCl and/or KCl) can be added to produce a dilute salt solution. Preferably, the salt is vacuum dried crystalline salt which is commercially produced to a consistent standard. The dilute salt solution can be a substantially constant concentration since a known quantity of salt is added to a known quantity of softened water to achieve a desired concentration of the dilute salt solution. Another method may involve mixing a known amount of a salt, such as, for example, NaCl or KCl, with de-ionized or de-mineralized water. This water can be used as delivered by a deionizer or demineralizer or can be dosed with a known amount of a buffering agent, such as, for example, sodium bicarbonate. This electrolyte can then be introduced to the production stage.

Figure 2:
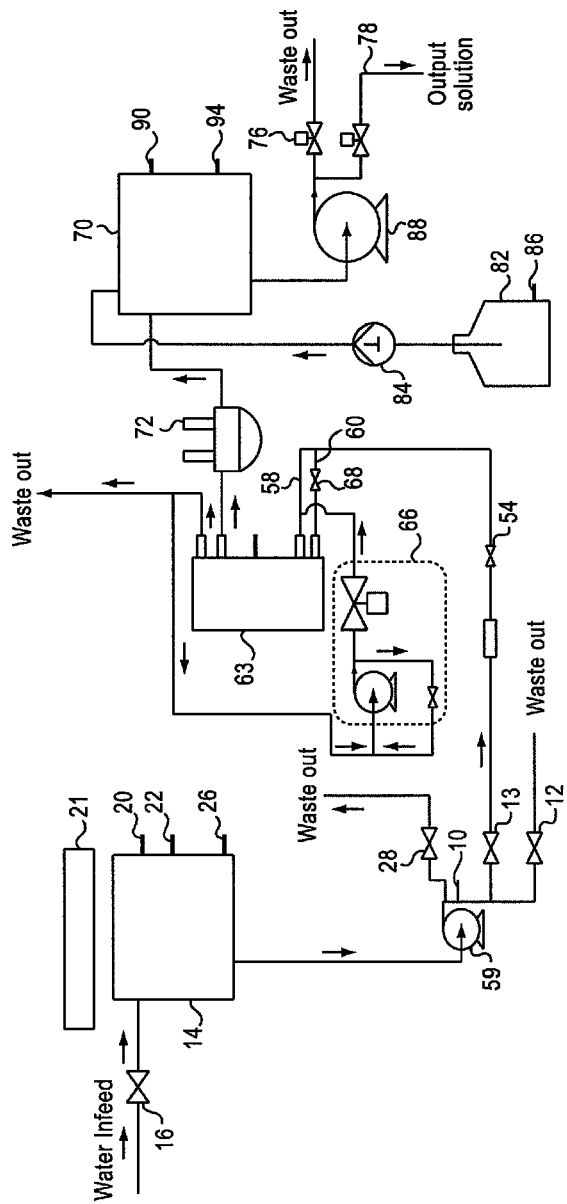
FIG. 2 is a flow diagram depicting the production of an electrolyzed saline solution for in accordance with certain embodiments of the present invention.
Figure 3:
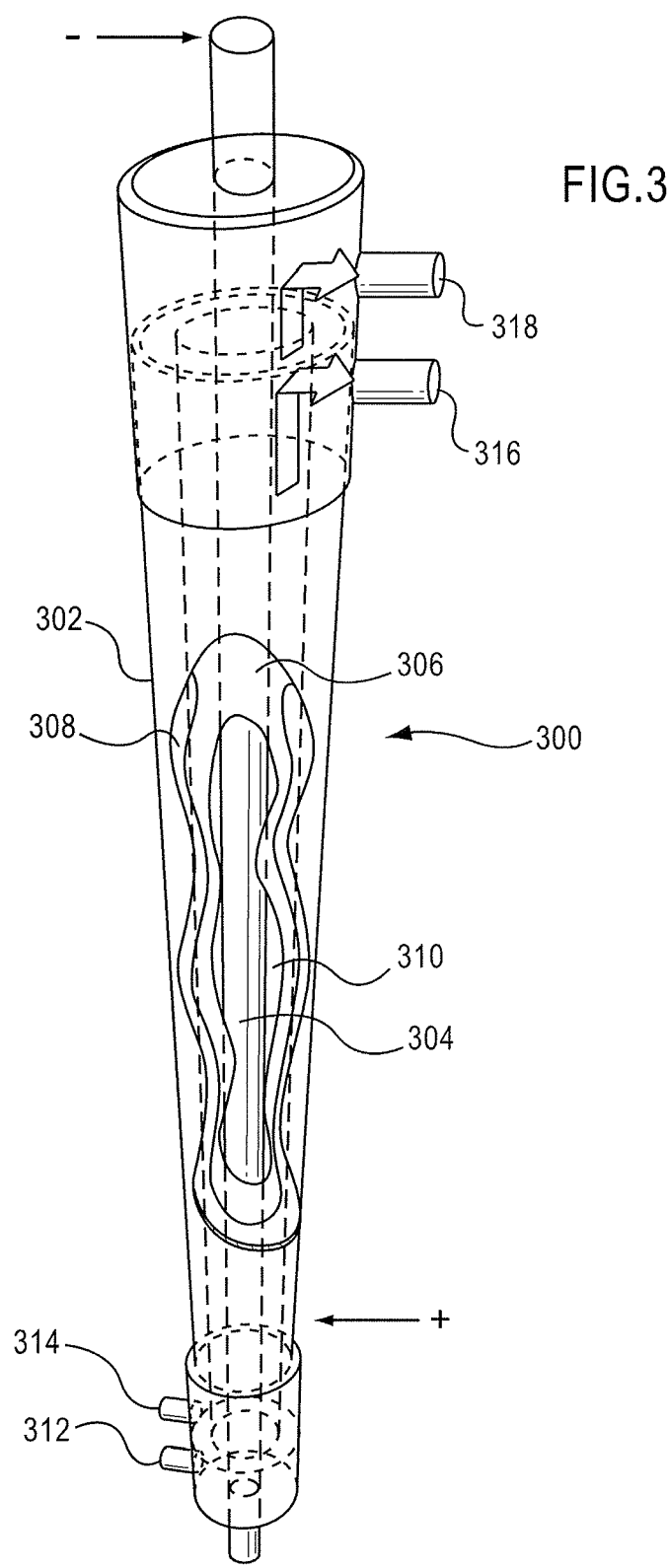
FIG. 3 is a schematic illustration of an electrochemical cell that may be used to produce an electrolyzed saline solution.

In the production stage, the dilute saline solution or prepared electrolyte can be passed to one or more electrolytic cell systems, such as the electrolytic cell pack 63 depicted in FIG. 2 (a preferred embodiment of which is described in more detail in FIG. 3). Of course, other electrolytic systems can be used as well such as parallel discs and parallel plate systems. The electrochemical cell includes a cathode and an anode chamber, across which a substantially constant electric current is applied. The applied electric current can be maintained constant via an energy control and monitoring zone. Catholyte and anolyte are produced from the cathode and anode chambers respectively as a result of electrochemical treatment of the saline solution in the cells. Catholyte and anolyte can be prevented from mixing using a separator. For example, a semi-permeable membrane can be used in the case of parallel plate technology (for example, NAFION® membrane) or a porous ceramic membrane. In some embodiments, the catholyte is not required for the final solution and is directed to drain. In other embodiments, all or part of the catholyte is re-introduced into the anode chamber (referred to in the art as catholyte recirculation). Catholyte that is not recirculated can be directed to waste, and anolyte, otherwise referred to as output solution, is passed to a buffer storage and quality subsystem in the storage and dispensing stage. The output solution can be tested in the buffer storage and quality subsystem, and, if it fails to meet the quality standards, can also be directed to waste. If the output solution falls within specification, the output solution can be permitted to pass to an output solution storage zone from where it can be subsequently dispensed for use or packaged.

FIG. 2 is a flow diagram or "hydraulic map" showing in more detail an exemplary method of producing an electrolyzed saline solution in accordance with the present invention. Potable water can be passed through an external water softener containing a cation exchange resin (not shown) thereby exchanging hardness ions of calcium and magnesium onto the resin and releasing sodium ions into the water. The softened water can be fed through a valve 16 into a softened water tank 14 which may include a plurality of level detectors for monitoring and controlling the softened water level. For example, tank 14 may include a level detector 20, which is a safety device which is activated only when the softened water in tank 14 reaches a predetermined extra high level to stop the charging of tank 14 with further softened water. Tank 14 may also include a level detector 22 which ensures that tank 14 has a correct volume of softened water to prepare the appropriate concentration of saline solution. Tank 14 may also include a level detector 26 and softened water will begin to re-charge tank 14 when the softened water drops below a predetermined low level determined by level detector 26 and at the end of production of one batch of electrolyzed saline solution. Tank 14 may also include a valve 28 which allows liquid to be drained.

To produce a saline solution from the softened water in tank 14, a salt, such as, for example, vacuum dried crystalline salt can be added to tank 14 via dispensing wheel 21. Dispensing wheel 21 contains many tablets of known salt mass, a pre-determined number of which are dispensed through a hole in the top of tank 14 at the start of each electrolyzed saline solution production cycle. Preferably, the saline solution has a salt concentration range of 2.0 to 90.0 g/L.

Pump 59 can pump the saline solution towards an electrolytic cell pack 63. The flow rate of the saline solution can be monitored by a sensor 10. The sensor can ascertain whether the incoming saline solution is at a temperature within the range under which the process can reasonably operate, such as between 5 and 35° C. Other parameters such as the incoming solution's pressure, softness, alkalinity, pH, conductivity, and microbial count can be monitored, modulated and/or controlled to establish that the solution falls within acceptable levels for the process or for desired characteristics of the resulting solution. For example, as the salt concentration of the solution is increased, the conductivity can be increased and other parameters, such as the current, would change. The various parameters can be modified to correspond to the desired salt concentration of the solution. A person of skill in the art can appreciate whether the incoming water is not suitable for processing according to embodiments of the present invention. If sensor 10 detects that the properties of the incoming saline solution do not fall within acceptable limits, the solution can be diverted through a waste discharge manifold (not shown) to a drain via valve 12. On the other hand, if the incoming saline solution is acceptable, it can be allowed to flow into the cells through valve 13.

The saline solution can then split into two streams 58 and 60 before being fed through electrochemical cell pack 63. In certain embodiments, electrochemical cell pack 63 can include eight electrolytic cells, with two sets of four cells connected hydraulically in parallel. For simplicity, only one cell is illustrated. In general, the number of cells in the cell pack can be determined by the output volume required from the particular system. Each cell has an anode chamber and a cathode chamber and the flow of saline solution can be split such that the greater portion is fed to the anode chamber and the lesser portion is fed to the cathode chamber. In certain embodiments, approximately 90% of the saline solution can be passed through the anode chamber and the remainder can be passed through the cathode chamber. The flow rate of saline solution through the cathode chamber can be much lower than for the anode chamber and the pressure in the cathode chamber can also be lower. The flow rate of saline solution into the cathode chamber, which also has an influence on the pH of the output solution, can be controlled by a flow regulator 68. Flow regulator 68 can be manually adjusted if there is a variation in input water quality.

In certain embodiments, the flow rate supplied to the anode is from 50% to 95%, inclusive of all intermediate values, of the solution applied to the electrolytic cell pack 63. In certain embodiments, the flow rate to the anode is from 85% to 95% of the solution supplied to the electrolytic cell pack.

As the saline solution flows through the electrolytic cells, a fixed current of from 0.1 to 25 amps, preferably 15 to 25 amps, and more preferably 18-19 amps, can be applied to each cell causing electrolysis of the saline solution thereby generating available free chlorine in the resulting anolyte, elsewhere generally referred to as the output solution. In order to produce output solution at a certain pH, for example between 5 and 7 (acidic to neutral), the pH of the output solution may be at least partially controlled by dosing a portion of the catholyte to the inlet stream for the anode chambers. The catholyte may be dosed to the inlet stream 58 by an adjustable pump and valve system 66 and the dosing rate is increased or decreased to achieve the target pH. The remaining catholyte which is not dosed into the input stream 58 for the anode chambers can be directed to waste, if necessary diluting it prior to disposal. As just described, in certain embodiments, the catholyte can be dosed into the anode stream 58 before this stream enters the anode. However, the catholyte can also be dosed into the anode stream after it has been electrolyzed. In those application where the electrolyte is prepared by mixing the various salts with de-ionized or de-mineralized water, mixing of the catholyte may not be performed, in which case all the catholyte is diverted to drain. If a proportion of the catholyte is used for pH control, then the catholyte can be dosed to the anode stream either before or after it enters the anode chamber.

The output solution can then be directed to tank 70. The pH of such output solution can be measured by a meter 72. If the pH does not fall within the desired parameters, a valve 76 can be opened and the contents of tank 70 can be drained to waste. Meter 72 can be linked to a pump and valve system 66 to adjust the level of catholyte dosed to the anode chambers thereby enabling the pH of the output solution to be adjusted to bring the output solution within the desired pH range. If the pH of the output solution is determined to fall within the desired parameters, valve 76 can be kept closed and the output solution can be allowed to fill tank 70. Other properties of the output solution, such as redox potential or AFC, could also form the basis of the measurement and control system consisting of meter 72 and adjustable pump and valve system 66.

Storage tank 70 may include various level detectors for monitoring liquid levels in the tank. For example, a level detector 90 may be activated by an extra high level of output solution within the tank, raising an alarm and stopping production. Low level detector 94 may be activated when the level of the output solution falls to a low level, raising an alarm and preventing further dispensing to the appropriate receptacle. As the output solution is dispensed and after a period of time below the level of detector 94, production of output solution may be re-commenced. From the storage tank, the output solution can be distributed in individual nebulizers, inhalers, or ampules. Where the electrolyzed solution is to be administered by humidifier or misting, the electrolytic cell system may be functionally coupled to a humidifier or fogger. Of course, the above-described processing steps of producing an electrolyzed saline solution are only exemplary and other electrochemical processes could be used to produce an electrolyzed saline solution of embodiments of the present invention.

FIG. 3 shows an embodiment of an electrolytic cell 300 used in certain methods of producing an electrolyzed saline solution according to an embodiment of the present invention. In this embodiment, cell 300 comprises co-axial cylindrical and rod electrodes 302, 304 respectively, separated by a semi-permeable ceramic membrane 306 co-axially mounted between the electrodes thus splitting the space between the electrodes to form two chambers 308 and 310. Cylindrical electrode 302, which is this embodiment forms the anode, is typically made from commercially pure titanium coated with a ruthenium oxide and iridium oxide-based electrocatalytic (active) coating suitable for the evolution of chlorine from a chloride solution. Rod electrode 304, which in this embodiment forms the cathode, is typically made from titanium and can be machined from an 8 mm stock bar to a uniform cross-section over its effective length, which is typically about 210 mm±0.5 mm. Of course, it will be understood by one of skill in the art that other suitable materials and configurations can be used to fabricate electrodes 302 and 304 to allow these electrodes to perform their necessary function. Also, either electrode can serve as the anode and similarly either electrode can serve as the cathode. If the rod is used as an anode, it is coated with a coating, such as ruthenium oxide and iridium oxide based electrocatalytic (active) coating, for example, suitable for the evolution of chlorine from a chloride solution. Semi-permeable ceramic membrane 306 forming a separator and creating the anode and cathode chambers 308 and 310 can be composed of aluminum oxide (80%), zirconium oxide (18.5%) and yttrium oxide (1.5%), and preferably has a porosity of about 50-70%, a pore size of 0.3 to 0.5 microns and a wall thickness of 0.5 mm+0.3 mm/−0.1 mm. The ceramic of certain embodiments of membrane 306 is described in the specification of patent application GB 2354478 (Sterilox Medical (Europe) Limited), the subject matter of which is incorporated herein by reference. Ceramic membrane 306 can be made of any other suitable semi-permeable or ion-selective material of ceramics other than the aluminum oxide, zirconium oxide and yttrium oxide ceramic described above.

Generally, the surface area of the anode can be largely defined by the quantities of output solution desired to be produced and available free chlorine content desired in that solution. However, in order to provide a system that is of a size appropriate for commercial installation and to produce the quantities of biocidal solution of the invention often required, an anode surface area of 0.065 to 0.095 m$^2$, inclusive of all intermediate values, can be utilized. Such a surface area can be made up by a number of electrolytic cells working in parallel. An anode area of 0.070 to 0.090 m$^2$ is more preferable, and an anode surface area of 0.075 to 0.085 m$^2$ is even more preferable. In certain embodiments, eight cells are arranged in parallel and the current density on the surface of each anode is within the range 1.5 to 2.5 kAm$^{-2}$, more preferably 1.7 to 2.2 kAm$^{-2}$, and still more preferably 1.85 to 1.95 kAm$^{-2}$.

In this embodiment, cell 300 is provided with entry passages 312 and 314 to permit the saline solution to enter cell 300 and flow upwards through the anode and cathode chambers 308 and 310 to be discharged as anolyte and catholyte through exit passages 316 and 318 respectively. The anolyte containing available free chlorine constitutes the output solution.

As previously described in reference to FIG. 2, in certain embodiments, in order to provide a preferred amount of output solution within a reasonable period of time, a group of cells can be connected together to form a cell pack 63. For example, a cell pack comprising eight cells connected together in parallel hydraulically and in series electrically may generate about 200 liters/hour of output solution.

When using higher volume generators, the flow rate through the anode chamber may vary between 100 to 220 l/h. For example, the flow rate may be 150 to 210 l/h, or may be 185 to 205 l/h is even more preferred. The flow rate can also be any value within the expressed ranges. Using lower volume generators, the flow rate through the anode chamber may be in the range of 10-50 l/h, such as, for example, 30 l/h. The person skilled in the art will appreciate that the flow rate can be altered beyond such a range but still produce the solution of embodiments of the invention by varying the number of cells/surface area of anode. For example, the flow rate per anode surface area of $1.25 \times 10^3$ to $2.75 \times 10^3$ lh$^{-1}$ m$^{-2}$ can be used produce an embodiment of an electrolyzed saline solution of the invention. The flow rate can also take any value with the aforementioned range. Preferably, the flow rate is $1.87 \times 10^3$ to $2.63 \times 10^3$ lh$^{-1}$ m$^{-2}$ and more preferably the flow rate is $2.31 \times 10^3$ to $2.56 \times 10^3$ lh$^{-1}$ m$^{-2}$. The skilled person can obtain the required current to produce a suitable solution by setting the flow rate to that just described and varying the current until the solution produced has the suitable specifications.

In certain embodiments, the current range is 15 to 25 A, inclusive of all intermediate values. In certain embodiments, a current range of 17 to 22 A is used and in certain embodiments a current range of 18.5 to 19.5 A is used.

The residual salt concentration of an embodiment of an electrolyzed saline solution can be from 2.0 g/l to 90 g/l. This residual salt concentration can result from the entire desired amount of salt being added during the input and pre-processing stage or less than the entire desired amount of salt being added during the input and pre-processing stage and the remainder of the desired amount of salt being added after the production stage.

Examples

Ocular Irritation

An eye irritation study was conducted on six healthy New Zealand white rabbits, free from evidence of ocular irritation and corneal abnormalities. The test article (0.1 ml hypochlorous acid, 689.5 ppm AFC) was placed into the conjunctival sac of one eye of each rabbit. The contralateral eye served as a control. The eyes were examined and scored by the Draize technique for any evidence of irritation or abnormalities of the cornea, on days 1, 2, and 3 post dose. The primary eye irritation score of each rabbit, each day was calculated. All eyes appeared normal at each observation period and there were no abnormal physical signs noted. In conclusion, under the test conditions of this study, hypochlorous acid (689.5 ppm AFC) showed no ocular irritation.

Dermal Irritation

A skin irritation study was conducted on six healthy New Zealand white rabbits. The test article (0.5 ml hypochlorous acid, 689.5 ppm AFC) was applied to one intact and one abraded site on the clipped back of each rabbit. Skin reactions were evaluated by the Draize technique at 24 and 72 hours after dosing and the primary irritation index was calculated. There was no erythema or edema noted at any time period and there were no abnormal physical signs noted during the observation period. In conclusion, under the test conditions of this study, hypochlorous acid (689.5 ppm AFC) showed no dermal irritation.

Skin Sensitization

A skin irritation study was conducted on ten test and five control albino guinea pigs. The method used was the Magnusson and Kligman guinea-pig maximization model. The animals were dosed (hypochlorous acid, 241-252 ppm AFC) by intradermal injection and by topical application. Following initial exposure to the test substance, the animals were subjected to approximately two weeks after topical induction to a "challenge" exposure of the test substance (50% v/v) in order to establish whether a hypersensitivity state had been induced. In this study, there was no evidence of delayed contact hypersensitivity. In conclusion, under the test conditions, hypochlorous acid (241-252 ppm AFC) demonstrated no skin sensitization.

Acute Oral Toxicity

A skin irritation study was conducted on ten fasted rats (five female and five male). No control animals were included in this study. All animals received a single oral gavage dose of the test substance (hypochlorous acid, 241-252 ppm AFC), at the dose level of 2000 mg/kg bodyweight. All animals were killed and examined microscopically at the end of the observational period, (Day 15). All animals were considered to have achieved satisfactory weight gain throughout the study. Macroscopic examination of animals on Day 15 revealed no abnormalities. In conclusion, under the test conditions of this study, hypochlorous acid (241-252 ppm AFC, 2000 mg/kg) demonstrated no oral toxicity.

Bacterial Mutagenicity

In vitro assessment of the mutagenic potential of hypochlorous acid (241-252 ppm AFC) was examined using histidine dependent auxotrophice mutants of *Salmonella typhimuium* (strains TA1535, TA1537, TA98 and TA100 and a tryptophan dependent mutant of *Escherichia coli* (strain CM891) were exposed to the test substance. Mutation assays were performed in the absence and presence of liver S9 fraction preparations from Aroclor 1254-induced rats. No evidence of mutagenic activity was observed with hypochlorous acid at the test concentration of 241-252 ppm.

In Vitro Microbiology Profile

Hypochlorous acid has rapid virucidal, bactericidal, sporicidal and fungicidal activity. It rapidly kills gram positive and gram negative bacteria, including antibiotic resistant species of MRSA and VRE. MRSA skin infections are becoming more prevalent and there is a perceived need for alternative medications for patients who are infected by MRSA. In vitro antimicrobial studies have shown hypochlorous acid to produce greater than log 5 kill within a 5 minute contact time against a range of wound pathogens including *S. aureus, P. aeruginosa, E. coli, Enterococcus* spp., and *Candida* spp., even at concentrations of ≤180 ppm of hypochlorous acid (Table 1), including activity against bacterial endospores.

Results demonstrate that hypochlorous acid solution, when generated by electrolysis, is effective in laboratory suspension and carrier tests within a 5 minute contact time against pathogens, including *Staphylococcus aureus, Escherichia coli, Pseudomonas aeruginosa, Enterococcus faecalis, Aspergillus* and *Candida albicans*.

TABLE 1

Exemplary pathogens killed by Hypochlorous acid 150-180 ppm, pH 6.3-6.75.

| Bacteria | Bacterial Endospores | Viruses | Fungi |
| --- | --- | --- | --- |
| *Pseudomonas aeruginosa* | *Bacillus cereus* | Adenovirus type V | *Aspergillus niger* |
| *Staphylococcus aureus* | *Bacillus subtilis* var *Clostridium sporogenes* | HIV-1 | *Candida albicans* |
| | | Poliovirus type 1 | *Trichophyton mentagrophytes* |
| | | Human Flu virus | |
| *Enterococcus faecium* (VRE) | | Orthopoxvirus | |
| | | Human Norovirus | |
| *Salmonella choleraesuis* | | Murine Norovirus MS2 coliphage virus | |

Bactericidal, Mycobactericidal, Fungicidal, Sporicidal, and Virucidal Suspension Tests Bactericidal activity suspension tests were performed using hypochlorous acid (at 180 ppm) against *Staphylococcus aureus* ATCC 6538 and *Pseudomonas aeruginosa* ATCC 15442 and *Enterococcus faecium* ATCC 10541. Stock culture of *Staphylococcus aureus* ATCC 6538, *Pseudomonas aeruginosa* ATCC 15442 and *Enterococcus faecium* ATCC 10541 were grown and maintained on Tryptic Soy Agar at 37° C. Bacterial suspensions (1 ml) were added to 1 ml of 0.3% BSA and 8 ml of hypochlorous acid at a range of concentrations at 20° C. After an exposure time of 5 minutes, 1 ml samples were neutralized using universal quench. All samples were serially diluted, plated out on Tryptic Soy Agar, incubated at 37° C. for 3 days and colonies forming units counted.

Fungicidal activity tests were performed using hypochlorous acid (140-180 ppm) against *Candida albicans* ATCC 10231 and *Aspergillus niger* ATCC 16404. Stock culture of *Candida albicans* ATCC 10231 and *Aspergillus niger* ATCC 16404 were grown and maintained on Malt Extract Agar at 30° C. Fungal suspensions (1 ml) were added to 1 ml of sterile distilled water and 8 ml of hypochlorous acid solution at a range of concentrations at 20° C. After an exposure time of 5 minutes, 1 ml samples were neutralized using standard quench solution. All samples were serially diluted, plated out on Tryptic Soy Agar, incubated at 37° C. for 3 days and colonies forming units counted.

Sporicidal activity tests were performed using hypochlorous acid solution against *Bacillus cereus* CIP 7803, *Bacillus subtilis* CIP 7718, *Clostridium sporogenes* CIP 7939. Stock spore suspensions of *Bacillus cereus* CIP 7803, *Bacillus subtilis* CIP 7718, *Clostridium sporogenes* CIP 7939 were obtained from the Pasteur Institute's National Collection for the Culture of micro-organisms. Spore suspensions (1 ml) were added to 4 ml of sterile distilled water and 5 ml of hypochlorous acid solution at a range of concentrations at 20° C. After an exposure time of 60 minutes, 1 ml samples were neutralized using standard quench solution. All samples were serially diluted, plated out on selective agar, incubated aerobically or anaerobically at either 30° C. or 37° C. for 72 hours and colonies forming units counted.

Virucidal activity tests were performed using hypochlorous acid against *Polio Enterovirus* 1 Sabin strain, *Adenovirus* type V and *Orthopoxvirus*. *Polio Enterovirus* 1, SABIN sock cultures were maintained on Vero cells, *Adenovirus*, type V, cultured on KB cells and *Orthopoxvirus* from the vaccine cultured on Vero cells. Viral suspensions (0.5 ml) were added to 0.5 ml of hypochlorous acid solution at a range of concentrations at 20° C. Viral suspensions were exposed to hypochlorous acid for 15, 30 and 60 minutes. Following incubation, all samples were serially diluted and viruses cultured according to standard procedures.

The effectiveness of hypochlorous acid against Norovirus (NV) and MS2 coliphage virus was evaluated using non-culturable human NV measured by RT-PCR and against two other surrogate viruses, coliphage MS2 and murine norovirus, detected by infectivity and RT-PCR. Norovirus, genetically characterized as genotype II.4. was obtained from patient's stools of an outbreak of gastroenteritis at the University of North Carolina campus in 2004. Stools were made into 1% stool suspensions in phosphate buffered saline (PBS, pH 7.5) on the day of an experiment. Bacteriophage MS2 was used as a surrogate for norovirus and cultivated using *E. coli* Famp (ATCC 700891). Murine norovirus a surrogate for human norovirus was obtained from the Skip Virgin lab in St. Louis and was cultivated by cell culture in Raw cells (ATCC TIB-71, Virginia, US). Virus suspensions (25 µl) consisting of 1% norovirus stool suspension and MS2 stock were treated with 1.2 ml of hypochlorous acid solution (20-200 ppm). After specified contact times, 25 µl of 6% sodium thiosulfate was added into 1.2 ml chlorine+virus solution to neutralize any residual hypochlorous acid activity.

Broth cultures of either *M. terrae* (ATCC 15755) and *M. avium* (ATCC 15769) were grown for up to 35 days at 35° C. Mycobacteria suspensions (1 ml) were added to 1 ml of 0.3% BSA and 8 ml of hypochlorous acid solution at a range of concentrations at 20° C. After an exposure time of 5 minutes, 1 ml samples were neutralized using standard quench solution. The plates were incubated for 4-5 weeks at 35° C. and colonies counted.

Results shows that hypochlorous acid (150-180 ppm) effectively kills all organisms tested in the suspension assays. Passes were achieved after 5 minutes contact time against *Pseudomonas aeruginosa, Staphylococcus aureus, Enterococcus faecium, Candida albicans, Aspergillus niger, Mycobacterium terrae* and *avium*. Passes were achieved after 60 minutes contact time against *Clostridium sporogenes, Bacillus subtilis* var. *niger, Bacillus cereus* endospores and 15 minutes contact time against Poliovirus Enterovirus 1, Adenovirus, type V, Orthopoxvirus from vaccine (Table 2). Additionally, suspension tests showed that exposure of human norovirus, murine norovirus and coliphage MS2 to hypochlorous acid solution at the dose range of 20-200 mg/L achieved 3 $\log_{10}$ reductions of both MS2 and human norovirus within a contact time of 20 seconds.

TABLE 2

Reduction in the number of surviving cells after a contact time of 5 mins at 20° C. ± 1° C.

| Test Organism | Test Pass Requirement Log reduction | Test Result Log Reduction |
| --- | --- | --- |
| *Pseudomonas aeruginosa* ATCC 15442 | $10^5$ in 60 min | $>10^5$ in 5 min |
| *Staphylococcus aureus* ATCC 6538 | $10^5$ in 60 min | $>10^5$ in 5 min |
| *Enterococcus faecium* ATCC 10541 | $10^5$ in 60 min | $>10^5$ in 5 min |
| *Candida albicans* ATCC 10231 | $10^4$ in 60 min | $>10^4$ in 5 min |
| *Aspergillus niger* ATCC 16404 | $10^4$ in 60 min | $>10^4$ in 5 min |
| *Bacillus cereus* CIP 7 803 | $10^6$ in 60 min | $>10^6$ in 60 min |
| *Bacillus subtilis* var. *niger* CIP 7 718 | $10^6$ in 60 min | $>10^6$ in 60 min |
| *Clostridium sporogenes* CIP 7 939 | $10^6$ in 60 min | $>10^6$ in 60 min |
| *Mycobacterium terrae* ATCC 15755 | $10^6$ in 60 min | $>10^5$ in 5 min |

TABLE 2-continued

Reduction in the number of surviving cells after a contact time of 5 mins at 20° C. ± 1° C.

| Test Organism | Test Pass Requirement Log reduction | Test Result Log Reduction |
|---|---|---|
| *Mycobacterium avium* ATCC 15769 | $10^6$ in 60 min | $>10^5$ in 5 min |
| Orthopoxvirus from vaccine | $10^4$ in 60 min | $>10^4$ in 15 min |
| Adenovirus, type V | $10^4$ in 60 min | $>10^4$ in 15 min |
| Poliovirus Enterovirus 1 | $10^4$ in 60 min | $10^4$ in 15 min |

Bactericidal, Fungicidal and Virucidal Carrier Tests

Carriers (glass slides) were inoculated with either *Salmonella cholerasuis, Pseudomonas aeruginosa* and Human influenza A, *Enterococcus faecium*, HIV, *Trichophyton mentagrophytes* or *Staphylococcus aureus*. These were then dried following the protocol guidelines and exposed to hypochlorous acid at <180 ppm for various contact times and cultured for viability.

For Norovirus and MS2 Coliphage Virus carrier tests, No. 4 polished stainless steel and ceramic tile were used as representative non-porous and porous surfaces, respectively. Virus suspensions (20 µl) consisting of 1% norovirus stool suspension (human Norovirus type II) and MS2 phage stock were spotted onto the center of each carrier surface in triplicate (i.e. three different squares per experiment). As a negative control, 20 µl of sterile PBS (pH 7.5) was spotted onto the carrier surface. The material was allowed to dry on each surface for 2-3 hours in a laminar flow hood. Individual surfaces were transferred with sterile forceps to 24 well plates. After specified contact times, 0.275 µl of 16% beef extract and 25 µl of 6% sodium thiosulfate were added into 1.2 ml chlorine solution to elute viruses and neutralize any residual hypochlorous acid activity. Plates were mixed for 20-minutes on a rotary device to facilitate virus elution from the test surfaces.

Tests passes (Table 3) were achieved after 2 minutes contact time against *Salmonella cholerasuis, Pseudomonas aeruginosa* and Human influenza A and after 5 minutes contact time *Enterococcus faecium*, HIV, *Trichophyton mentagrophytes* and *Staphylococcus aureus*. Additionally, carrier test results showed that hypochlorous acid on ceramic tiles and stainless steels inactivated MS2 and human norovirus by >3 $\log^{10}$ based on infectivity alone and infectivity and RNA testing, after 1 min of contact time with hypochlorous acid (20-200 ppm).

TABLE 3

| Carrier Test Data | |
|---|---|
| Microorganism | Time to achieve pass |
| HIV-1 | 5 min |
| *Enterococcus faecium* (VRE) | 5 min |
| *Pseudomonas aeruginosa* | 2 min |
| *Staphylococcus aureus* | 5 min |
| *Salmonella choleraesuis* | 2 min |

TABLE 3-continued

| Carrier Test Data | |
|---|---|
| Microorganism | Time to achieve pass |
| *Trichophyton mentagrophytes* | 5 min |
| Human Influenza A | 2 min |

Modifications of the disclosed embodiments incorporating the spirit and substance of the invention may occur to persons skilled in the art and such modifications are within the scope of the present invention. All references cited herein are incorporated by reference in their entirety.

What is claimed is claim:

1. A method for treating a condition characterized by chronic type I or type IV hypersensitivity, comprising: administering to a patient in need thereof one to four times daily an effective amount of a hypochlorous acid composition to an affected region sufficient to maintain the hygiene of the affected region,
   wherein the composition is produced by electrolysis of saline, and
   wherein the composition has an available free chlorine content of from 20 to 1000 ppm that is at least 90% hypochlorous acid relative to the total concentration of hypochlorous acid, hypochlorite, and $Cl_2$.

2. The method of claim 1, wherein the condition is a condition of the eye, ear, nose, mouth, or throat.

3. The method of claim 2, wherein the ocular condition includes conjunctivitis, blepharitis, external hordeolum, internal hordeolum, uveitis, canaliculitis, and/or dacrocystitis.

4. The method of claim 1, wherein the hypochlorous acid has a pH of from 4 to 7.

5. The method of claim 1, wherein the hypochlorous acid has an available free chlorine content of above 200 ppm.

6. The method of claim 4, wherein the available free chlorine consists essentially of hypochlorous acid as an active agent.

7. The method of claim 1, wherein the condition involves one or more of rhinitis, rhinorrhea, nasal congestion, otitis media, external otitis, pharyngitis, and stomatitis.

8. The method of claim 1, wherein the condition is delayed-type hypersensitivity.

9. The method of claim 1, wherein the condition is immediate-type hypersensitivity.

10. The method of claim 1, wherein the composition is the form of a cream, gel, foam, aerosol, or solution.

11. The method of claim 1, wherein the composition is administered to the skin.

* * * * *